(12) United States Patent  (10) Patent No.: US 6,736,783 B2
Blake et al.                (45) Date of Patent:     May 18, 2004

(54) AUTOMATED BLOOD SAMPLING APPARATUS

(75) Inventors: Kevin R. Blake, Green Brook, NJ (US); Kang Cheng, Bridgewater, NJ (US); Glenn A. Clarke, Flemington, NJ (US); Gary S. Kath, Scotch Plains, NJ (US); Gregory W. King, Carteret, NJ (US); Tsuei-Ju Wu, East Brunswick, NJ (US)

(73) Assignee: Merck & Co., Inc., Rahway, NJ (US)

( * ) Notice: Subject to any disclaimer, the term of this patent is extended or adjusted under 35 U.S.C. 154(b) by 603 days.

(21) Appl. No.: 09/808,449

(22) Filed: Mar. 14, 2001

(65) Prior Publication Data

US 2001/0031932 A1 Oct. 18, 2001

Related U.S. Application Data

(60) Provisional application No. 60/196,744, filed on Apr. 12, 2000.

(51) Int. Cl.[7] ............. A61B 5/00; A61F 2/02; A61M 1/00
(52) U.S. Cl. ............... 600/582; 604/327; 600/575
(58) Field of Search ................. 600/582, 573, 600/575, 578, 579, 576; 604/328, 329, 330, 327, 317; 424/94; 435/4; 206/364

(56) References Cited

U.S. PATENT DOCUMENTS

| 4,029,767 A | * | 6/1977  | Vairel et al. ........... 424/94.3 |
| 4,360,016 A | * | 11/1982 | Sarrine ................. 600/576 |
| 4,817,632 A | * | 4/1989  | Schramm ............... 600/582 |
| 4,931,044 A | * | 6/1990  | Beiter .................. 604/248 |
| 5,865,766 A | * | 2/1999  | Bonsall et al. .......... 600/578 |
| 6,001,067 A | * | 12/1999 | Shults et al. ........... 600/584 |
| 6,102,872 A | * | 8/2000  | Doneen et al. .......... 600/582 |
| 6,485,428 B1 | * | 11/2002 | Enk .................... 600/487 |
| 6,533,734 B1 | * | 3/2003  | Corley et al. ........... 600/573 |
| 6,540,675 B2 | * | 4/2003  | Aceti et al. ............ 600/309 |

* cited by examiner

Primary Examiner—Thomas Denion
Assistant Examiner—Daniel Robinson
(74) Attorney, Agent, or Firm—James M. Hunter, Jr.; Mark R. Daniel

(57) ABSTRACT

An apparatus and process for automatically, repetitively sampling blood from conscious animals. The apparatus can simultaneously extract blood from a number of conscious, catherized animals at programmable time intervals. The apparatus is characterized as a system of computer controlled valves and pumps connected by tubing filled with saline solution to a catherized animal. Blood samples are collected via a cannula from the animal and placed in a fraction collector for analyses.

26 Claims, 10 Drawing Sheets

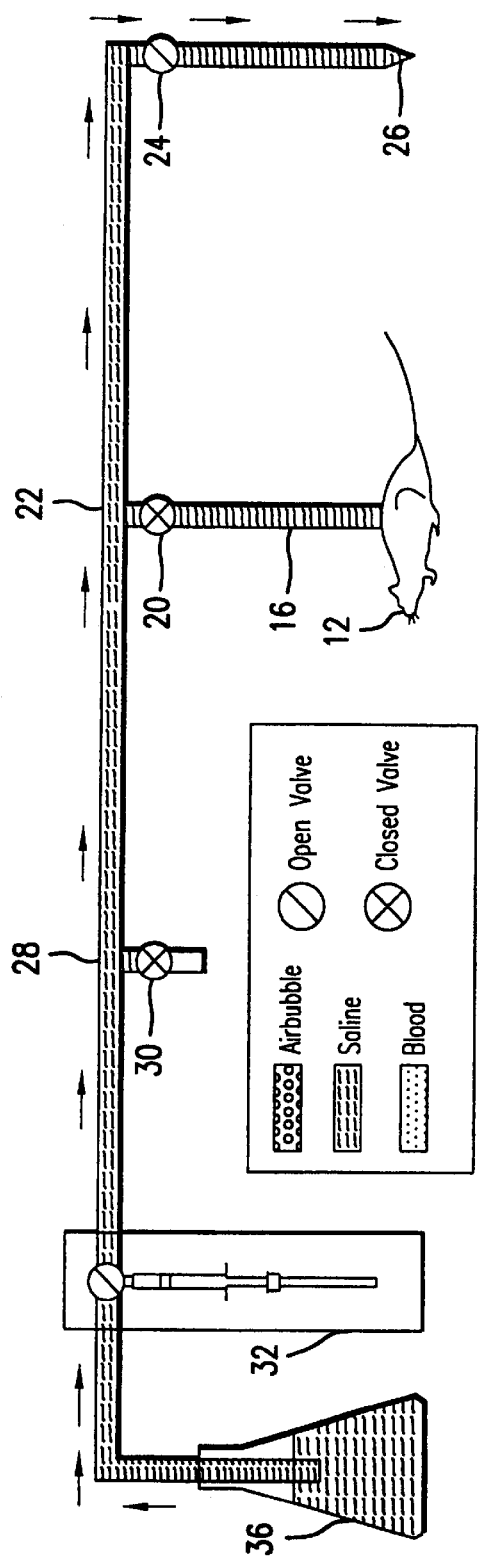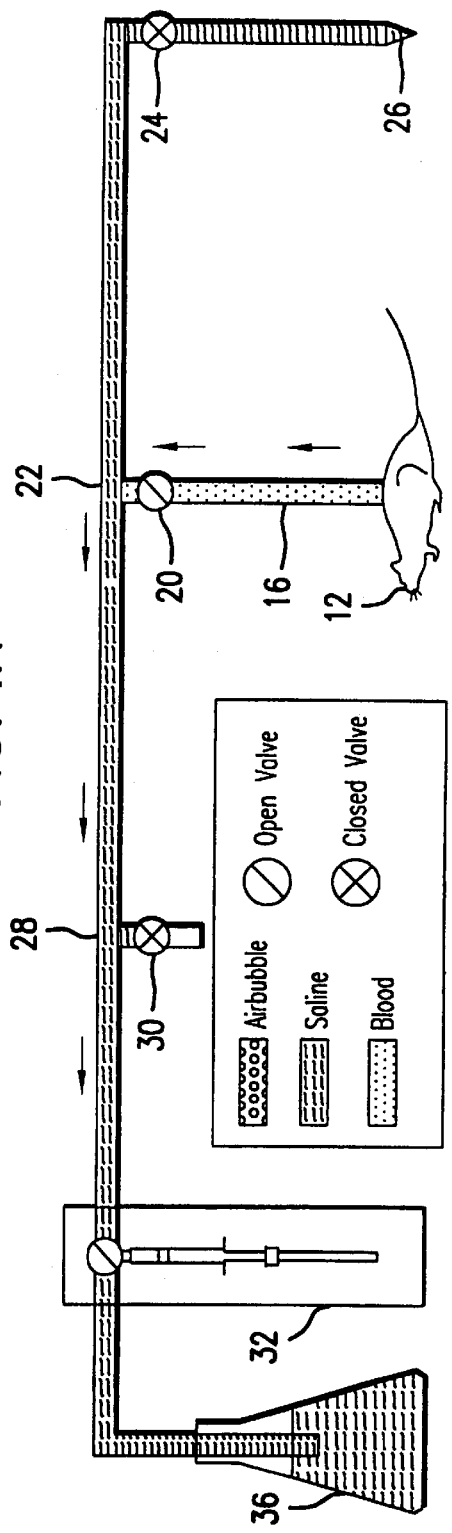
FIG. 4A
FIG. 4B

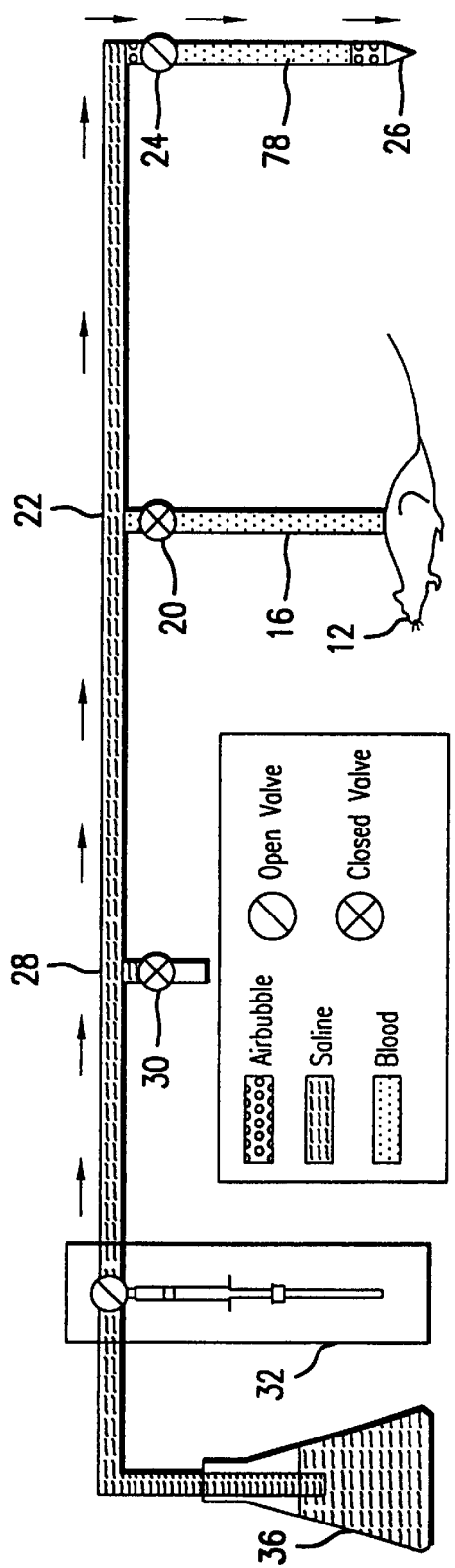
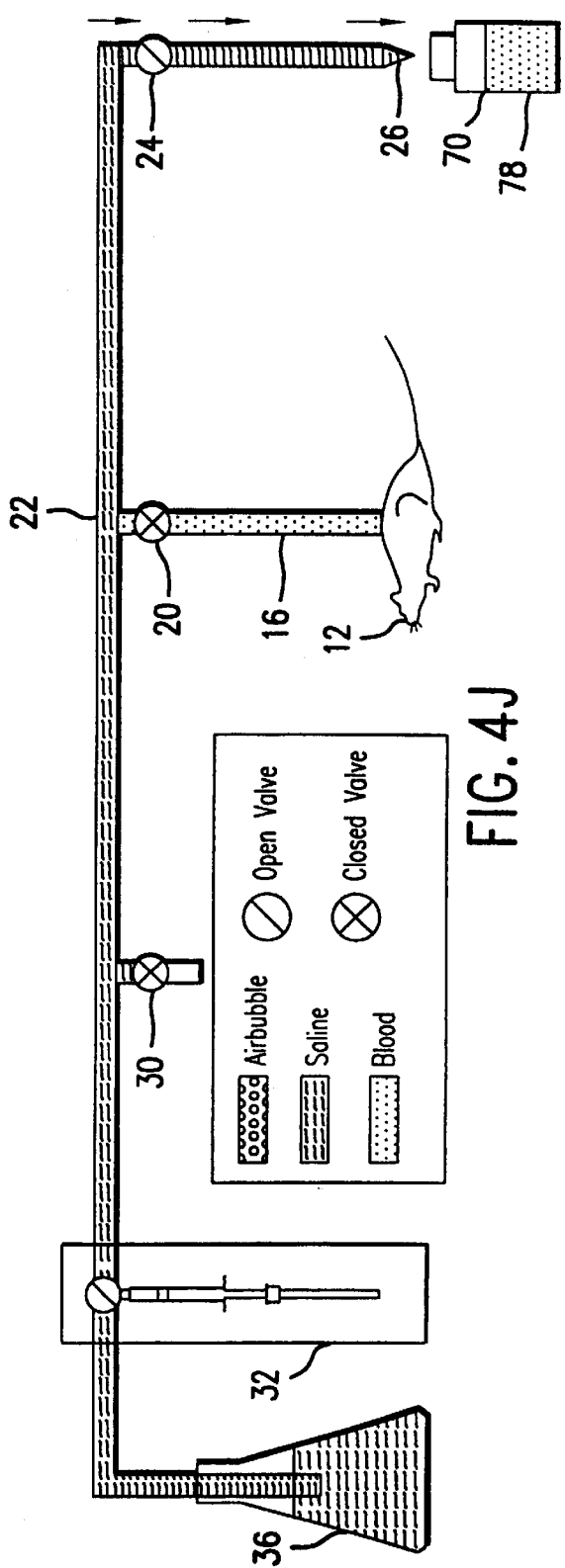
FIG. 4I
FIG. 4J

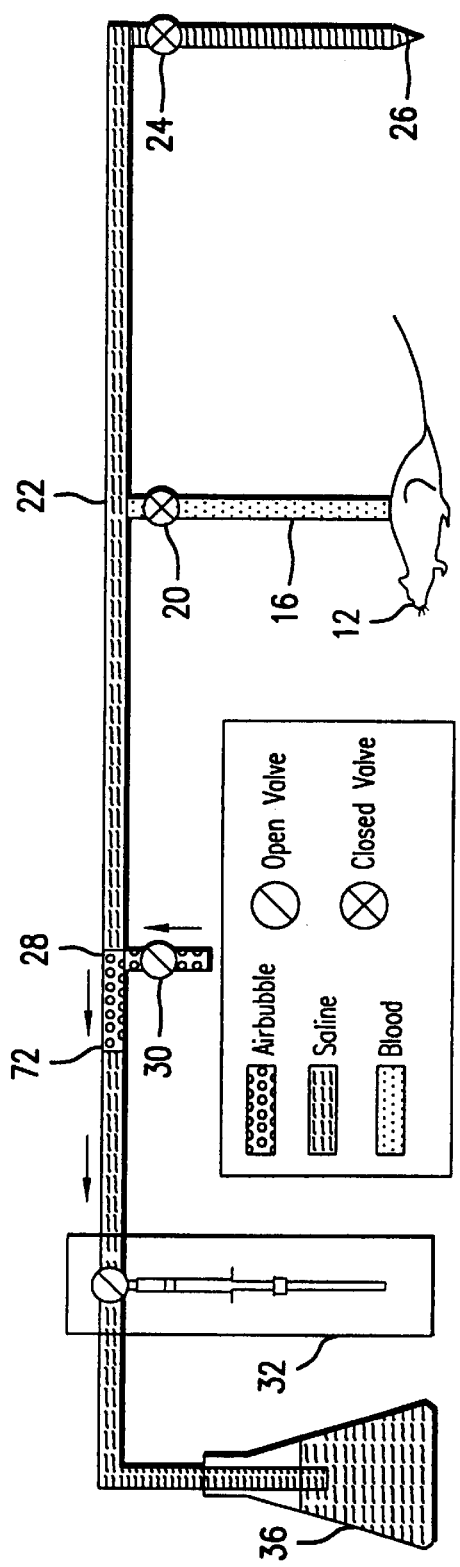
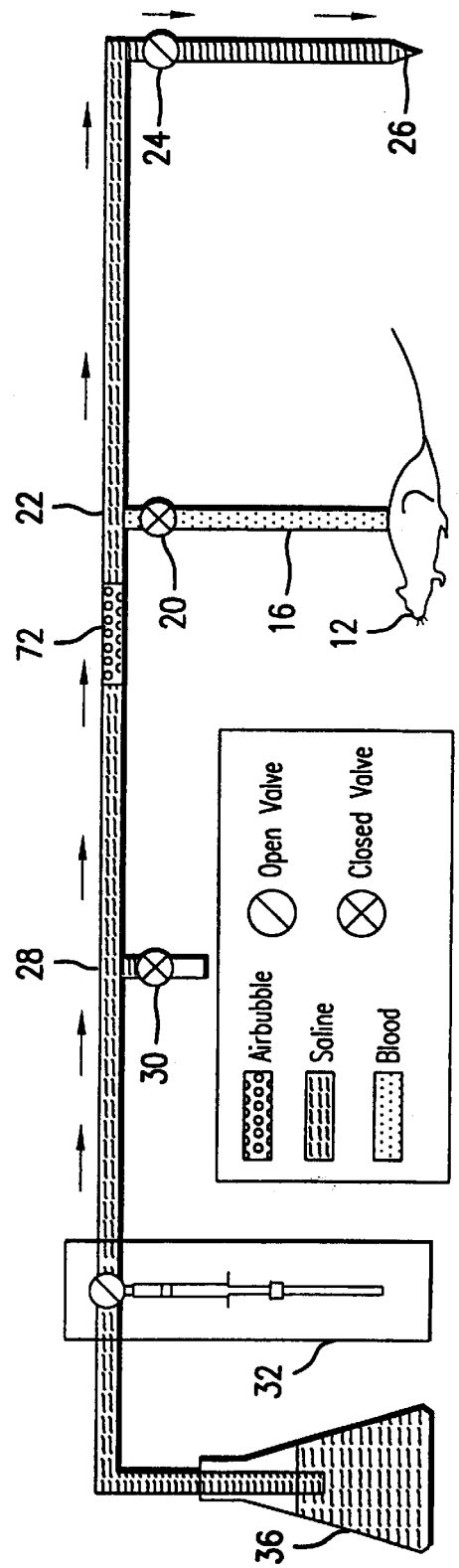

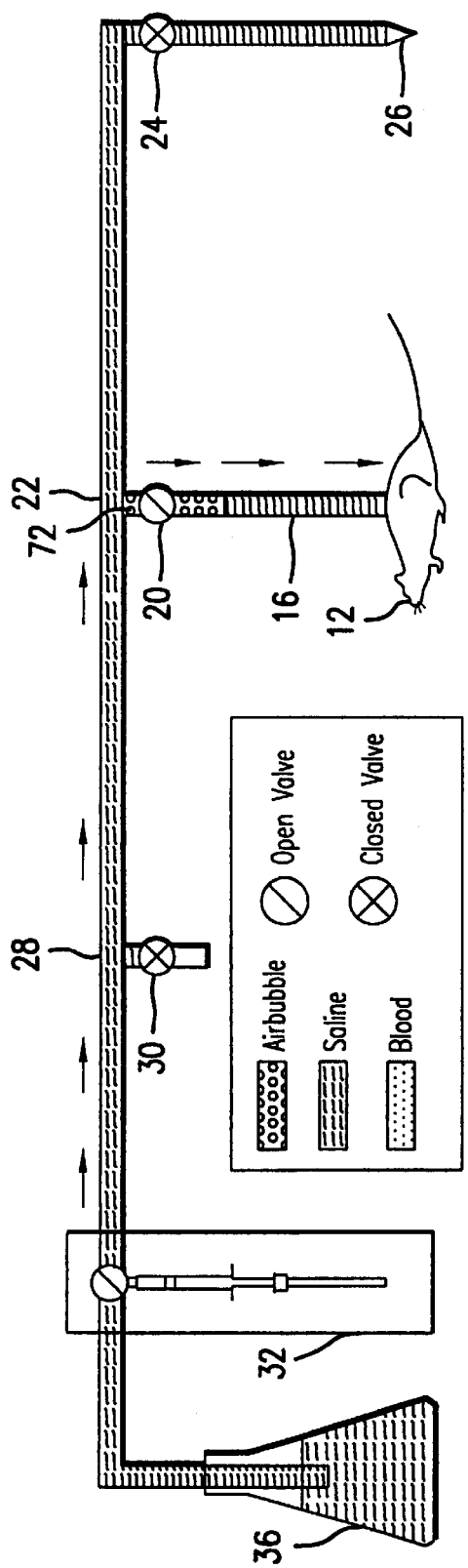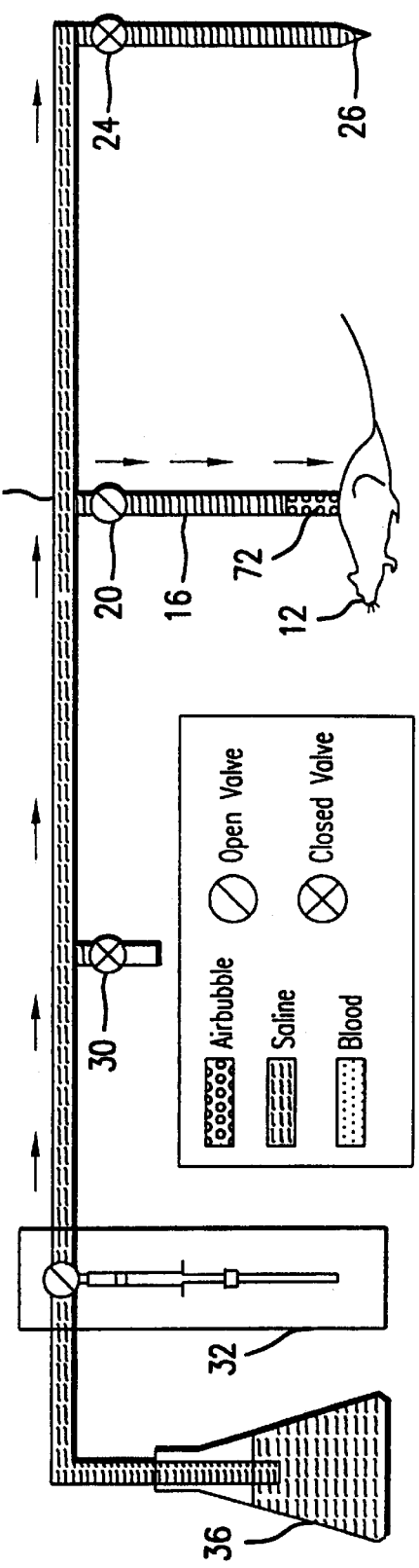
FIG. 4M
FIG. 4N

AUTOMATED BLOOD SAMPLING APPARATUS

This application claims the benefit of Provisional Application No. 60/196,744, filed Apr. 12, 2000.

BACKGROUND OF THE INVENTION

The removal or extraction of blood from conscious animals has been utilized to determine the presence of bacteria, hormones, parasites, toxins, as well as the metabolism of drugs and other substances in the animal. Heretofore, the removal of blood from animals has been performed manually or on an as necessary basis. Therein, the cannulized animal is anaesthetized and the sample is collected as required at intermittent time intervals with a syringe.

A system for automatic collection of small samples of blood from conscious animals has been described (Clark, R. G. et al, "Automated Repetitive Microsampling Of Blood: Growth Hormone Profiles In Conscious Male Rats," J. Endocr. (1986) Vol. 111, pp. 27–35). Therein rats bearing indwelling intravenous catheters were connected via swivels to a solenoid operated, three-way fitting and tubing to a multi-channel peristaltic pump, valves and a fraction collector. The tubing was filled with heparinized saline from a reservoir. Blood samples from the rats are drawn past the three-way fitting using a peristaltic pump. A small portion of the blood is pushed past the three-way fitting into a collector and the remainder of the sample is returned to the animal. This system, particularly, if the animal is small, fails to address the problem of a replacement substance for the animal's blood that has been removed. The reference further fails to suggest a solution for the problem of contamination of the blood sample with saline solution or excess dilution of sample therewith.

There is now a need for an automated blood sampling system that can sample blood from a conscious animal and address the problems of replacement of sampled blood to maintain the animals metabolism. There is a further need to address the problem of contamination and excess dilution of the blood sample with heparinized saline solution. The present invention addresses and resolves the problems associated with the automatic blood sampling system described herein above.

SUMMARY OF THE INVENTION

The present invention is directed to an apparatus for automatically, repetitively sampling blood from a conscious animal, characterized as:

a) means for confining a conscious, catheterized animal;
b) a cannula having first and second ends, said first end connected to the catherized animal, said cannula being suitable for sampling blood from the animal;
c) a cannula valve having first and second ends, said first end connected to the cannula, said cannula valve opening and closing being computer controlled;
d) a cannula T-fitting having first, second and third ends, said first end connected to the second end of the cannula valve;
e) an outlet valve having first and second ends, said first end connected, via tubing, to the second end of the cannula T-fitting, said outlet valve opening and closing being computer controlled;
f) a dispensing tip having first and second ends, said first end connected to the second end of the outlet valve, said second end being suitable for discharging blood into a sample, collection vial;
g) means for horizontal and vertical movement of the dispensing tip, said means for movement being computer controlled;
h) an air T-fitting having first, second and third ends, said first end connected to the third end of the cannula T-fitting;
i) an air valve having first and second ends, said first end connected to the second end of the cannula T-fitting, said second end exposed to the check valve;
j) a syringe pump suitable for transferring blood and saline through the apparatus, said pump having first and second ends, said first end connected, via tubing, to the third end of the air T-fitting, said pump being computer controlled;
k) a rotary, programmable valve having four ports for receiving and discharging fluids, wherein the ports open and close by computer control, said first port being connected, via tubing, to the second end of the syringe pump;
l) a heparinized saline source, said saline source connected to the second port of the programmable valve;
m) a fraction collector, comprising:
  i) a base having two horizontally, opposed, parallel tracks, and a single track horizontally positioned above and perpendicular to the horizontally opposed, parallel tracks,
  ii) a temperature controlled rack in slidable contact with the horizontally opposed, parallel tracks,
  iii) means for sliding the rack along the tracks, said means being computer controlled, and
  iv) a plurality of sample, collection vials removably located in the rack, said vials being suitable for receiving samples from the dispensing tip; and
n) computer means for accepting timing commands for collecting samples from the animal in coordination with the opening and closing of valves, sliding of the temperature controlled rack, pumping of the syringe pump, and dispensing samples into the collection vials, wherein samples can be collected at predetermined time intervals.

The invention is also directed to a process for automatically collecting samples from a conscious animal utilizing the apparatus described herein.

DETAILED DESCRIPTION OF THE INVENTION

The invention described herein is directed to an apparatus for automatically, repetitively sampling blood from a conscious animal. The various components of the apparatus, i.e. valves, pump and vacuum means, and fraction collector, can be computer controlled and programmed to collect samples from the animal at prescribed times.

Figure 1:
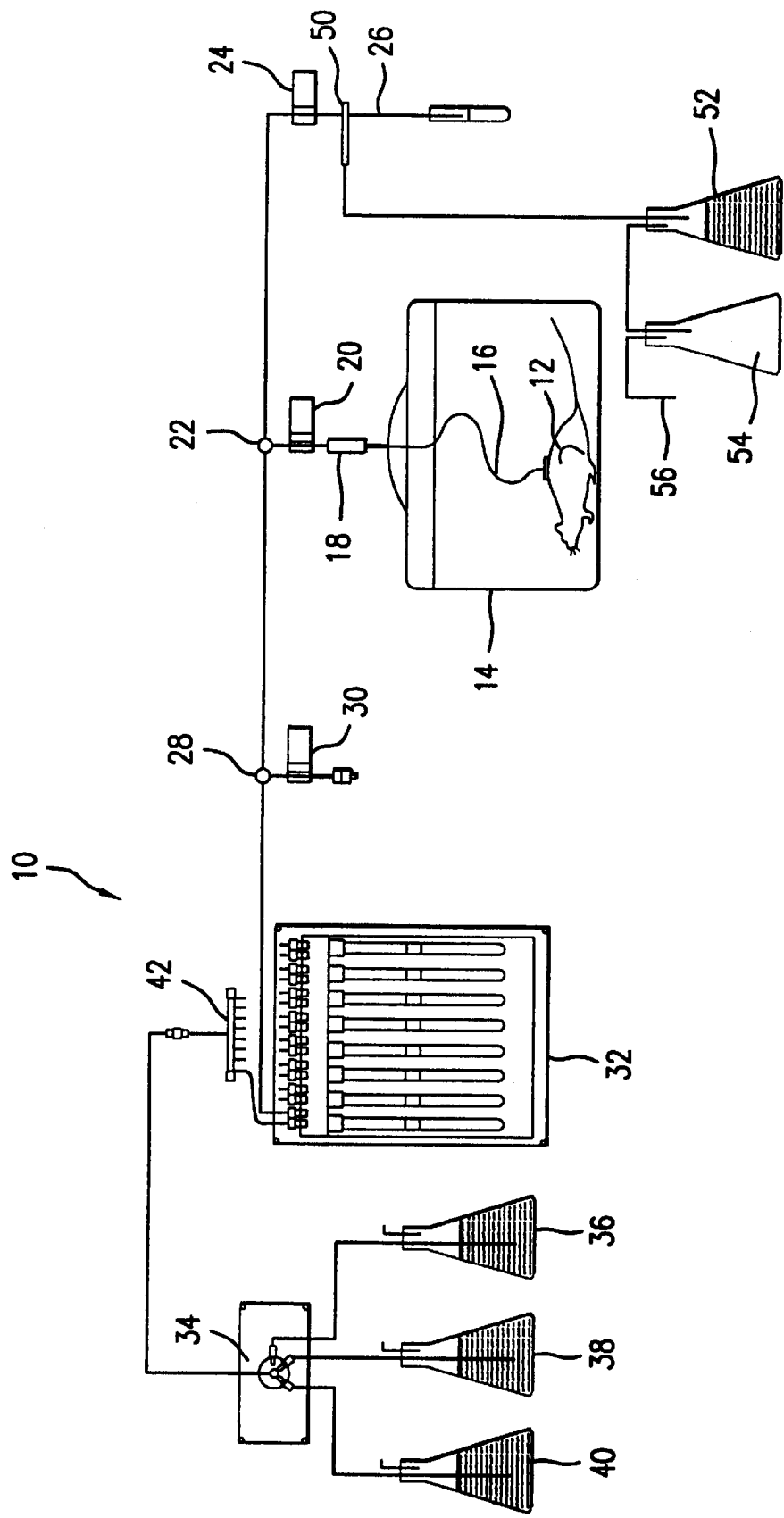
FIG. 1 illustrates a front view in elevation of the automatic blood sampling apparatus.

Referring to FIG. 1, apparatus (10) is characterized as a series of automated components, i.e. valves, fittings and pumps, connected by flexible or rigid tubes, wherein many of the components being computer controlled. An animal (12) to be sampled is confined to metabolic cage (14) with ample food and water. After the animal is anaesthetized, a catheter containing heparinized saline solution is implanted into a vein thereof. The catheter is then exteriorized via an intravenous cannula (16), and the cannula connects to swivel (18) to allow free movement of the animal within the cage. The swivel connects, via flexible tubing, to cannula valve (20), wherein the opening and closing of the valve is computer controlled. The cannula valve connects, via flexible tubing, to a three-port, cannula T-fitting (22). A second end of the cannula T-fitting connects, via flexible tubing, to outlet valve (24), wherein the opening and closing of the valve is computer controlled. The outlet valve connects to rigid, dispensing tip (26). Typically, the outlet valve and the dispensing tip are positioned on a computer controlled, base (not shown) for reciprocating, vertical movement. A third end of the cannula T-fitting connects, via flexible tubing, to three-way, air T-fitting (28). The air T-fitting connects to air valve (30) and the air valve connects to an ambient atmosphere inlet, optionally via a check valve. Air T-fitting (28) is further connected, via flexible tubing, to syringe pump (32) that provides means for transfer of fluids through various tubing and components of the apparatus. The syringe pump connects to a port of multi-port, programmable valve (34). The other ports of the programmable valve are connected to saline-containing source (36), distilled water source (38), and acid wash source (40), respectively. Generally, the cannula and outlet valves can be selected from pinch and check valves, as well as other suitable valves known in the art.

Optionally, depending upon the number of animals to be sampled, optionally, a plurality of blood sampling lines can be incorporated into the apparatus. Referring to FIG. 1, a plurality of blood sampling lines characterized as components (14) through (28), components (52) through (56), and associated tubing, can be connected via syringe pump (32) to syringe pump manifold (42). Syringe pump manifold (42) connects the plurality of syringe pumps to programmable valve (34). The programmable valve facilitate common filling and flushing of the lines with saline solution, acid solution, and distilled water.

An additional feature of the invention is a vacuum system to assist in flushing the apparatus components and tubing of unwanted fluids. Referring to FIG. 1, the vacuum system is illustrated as dispensing tip manifold (50) connected, via flexible tubing, to waste trap (52). Waste trap (52) connects, via flexible tubing, to safety trap (54) that connects, via flexible tubing, to vacuum means (56). Dependent upon the number of blood sampling lines incorporated into the apparatus, the vertically reciprocating base containing the dispensing tips and outlet valves can be fitted with a dispensing tip manifold to facilitate the removal of waste fluids from the apparatus. For a plurality of dispensing tips, the horizontal base of the manifold will contain a plurality of vertical holes therethrough, wherein each tube is adapted to vertical movement through the hole. A vertical hole, intersecting each of the horizontal holes connects to a vacuum means through a waste trap. During removal of waste fluids from the apparatus, via the dispensing tip, the discharge end of the tubes are moved proximal to the vertical holes in the manifold, the vacuum means applied, and the waste fluids are drawn through the horizontal hole intersecting each vertical hole into the waste trap. The tubing connections to the waste trap should be maintained in a space above the waste fluids to prevent fluid take-up into the vacuum means. During operation of the blood sampling apparatus, after the dispensing tip moves vertically, proximal to the first hole of the dispensing tip manifold and the vacuum means activated, any waste fluids in the tubing can be evacuated therefrom into the waste collection trap. The valve is closed and vacuum means are applied, via computer controls, and any blood or other liquids within the line between the dispensing valve and the end of the dispensing tip can be evacuated therefrom by application of the vacuum.

Figure 2:
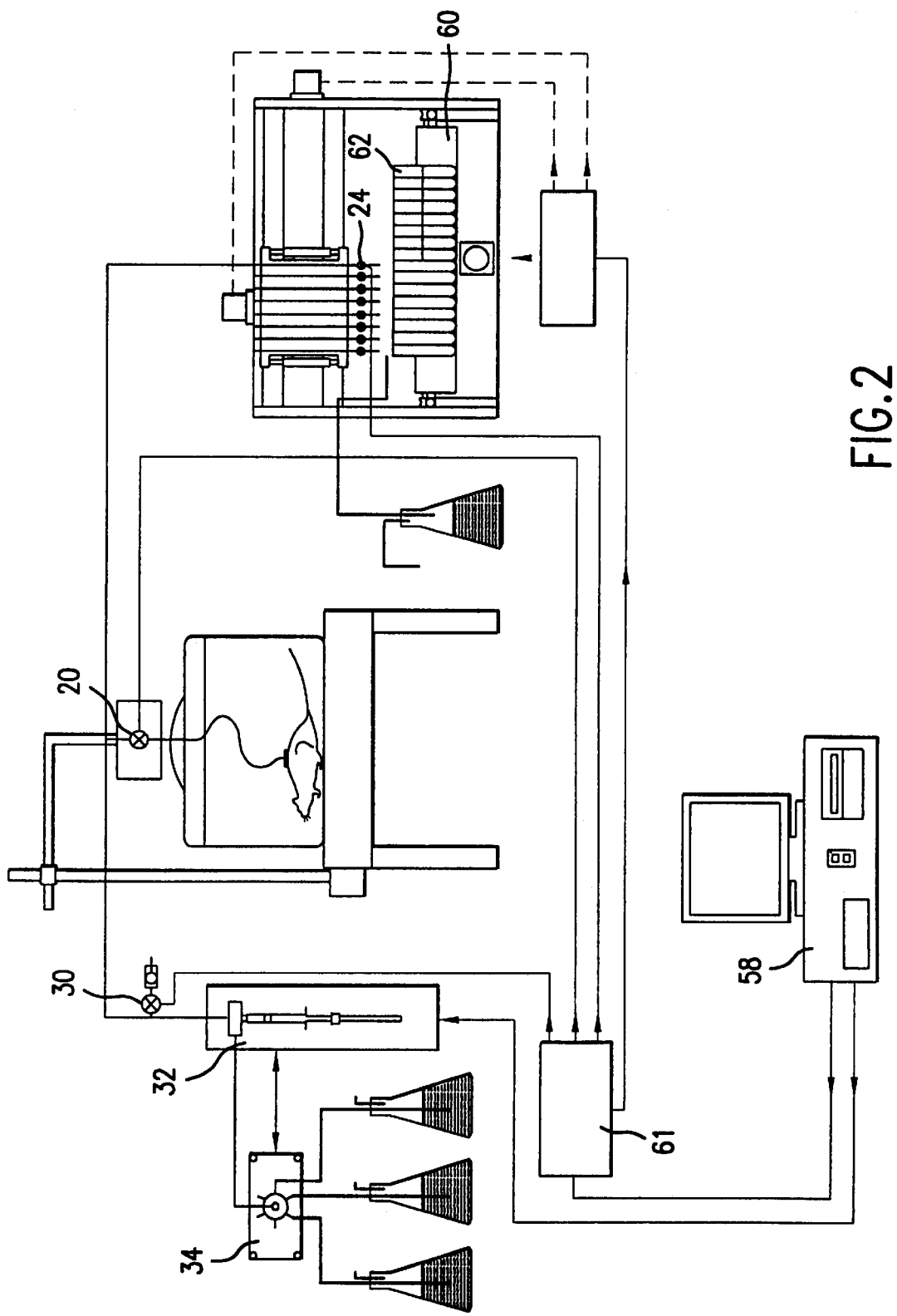
FIG. 2 illustrates a front view in elevation of the automatic blood sampling apparatus with computer means for controlling a process of sampling blood.

Referring to FIG. 2, fraction collector (60), holding sample collection vial (62), is illustrated as capable of sliding movement in one direction. The fraction collector is a temperature controlled, rack that positions the blood collection vials underneath the dispensing tip for collection of blood samples. Typically, the fraction collector will contain a heat exchanger for maintaining a constant vial temperature. The collector also contains a computer controlled motor means for movement of the collector.

Further illustrated in FIG. 2 is a process control scheme (shown by dotted lines) for connecting the components of the apparatus to computer control means (58). Digital input/output and fraction collector controller (61) are electronically connected to each of cannula valve (20), outlet valve (24), and air valve (30). The fraction collector's motor means is interfaced with controller (61) to provide computer controlled sliding of the collector rack in coordination with the discharge of samples from the dispensing tip into collection vials. Syringe pump (32), programmable valve (34) and vacuum means (54) are directly interfaced and controlled by computer means. The computer means is capable of coordinating and sequencing the opening and closing of the valves, fraction collector, syringe pump, and programmable valve to facilitate the repetitive, systematic sampling of blood, and cleaning of the apparatus at desirable times.

In one preferred embodiment of the invention there is described an apparatus for automatically, repetitively sampling the blood of a plurality of conscious animals, each animal being connected to a separate sampling line within a multi-line apparatus, characterized as:

a) means for individually confining a plurality of conscious, catheterized animals;

b) a plurality of cannulae, each cannula having first and second ends, said first end connected to the catheterized animal;

c) a plurality of cannula valves, each valve having first and second ends, said first end connected to the cannula, said cannula valves' opening and closing being computer controlled;

d) a plurality of cannula T-fittings, each valve having first, second and third ends, said first end being connected to the second end of each cannula valve;

e) a plurality of outlet valves, each valve having first and second ends, said first end being connected to the second end of each cannula T-fitting, said outlet valves' opening and closing being computer controlled;

f) a plurality of dispensing tips, each tube having first and second ends, said first end being connected to the second end of each outlet valve, said second end being suitable for discharging blood into a sample, collection vial;

g) means for horizontal and vertical movement of the dispensing tips in and out of the collection vial, said means for movement being computer controlled;

h) a plurality of air T-fittings, each valve having first, second and third ends, said first end being connected to the third end of the cannula T-fitting;

i) a plurality of air valves, each valve having first and second ends, said first end being connected to the second end of each air T-fitting, said air valves' opening and closing being computer controlled;

j) a plurality of syringe pumps, each pump having first and second ends, said first end being connected to the third end of each air T-fitting, wherein the pumps are suitable for pumping blood and saline through the apparatus, said pumps being computer controlled, wherein each series of a) through j) components comprise a separate sampling channel within the apparatus;

k) a rotary, multi-port, programmable valve, each port suitable for receiving and discharging fluids, said first port being connected to the second end of the syringe pump, optionally the second end of a plurality of syringe pumps connected to a first end of a common manifold having first and second ends, and the second end of the manifold connected to the first port of the programmable valve, each port's opening and closing being computer controlled;

l) a saline solution source connected to the second port of the programmable valve;

m) a fraction collector, comprising:
  i) a base having two horizontally opposed, parallel tracks, and a single track horizontally located above and perpendicular to the horizontally opposed, parallel tracks,
  ii) a temperature controlled rack in slidable contact with the horizontally opposed, parallel tracks,
  iii) means for sliding the rack along the tracks, said means for sliding the rack being computer controlled, and
  iv) a plurality of sample, collection vials removably arranged in the rack, said sample collection vials being suitable for receiving blood from the dispensing tip; and n) computer control means for programming and coordinating the operation of the collector, valves and pumps to collect blood samples at desired intervals, wherein the valves, syringe pump, and fraction collector functions are coordinated and controlled by the computer means to withdraw samples from the animal at repetitive, programmable intervals and discharge the samples in collection vials.

The blood sampling apparatus of the invention also contemplates a wash and rinse system. The system is characterized as water and acid wash sources connected to the third and fourth ports, respectively, of the programmable valve. The acid wash source is useful for cleaning the valves and tubing of residue after several collection cycles have been completed. After an acid wash cycle has been completed, a water rinse of the valves and tubing is necessary to remove any residual acid and neutralize the pH of the apparatus. During cleaning operations, the programmable valve closes the second port, connecting the saline source, and opens the fourth port, connecting the acid wash source, while the first port remains open. After completing the acid wash cycles to clean the system, one or more water, rinse cycles are performed to remove any residual acid from the components of the system. The acid wash and distilled water rinse cycles can be performed. For a complete cleaning of the apparatus, any animals should be removed. Typically, after completely rinsing the apparatus, distilled water is inserted into the tubing and valves until the next blood sample is collected.

Figure 3:
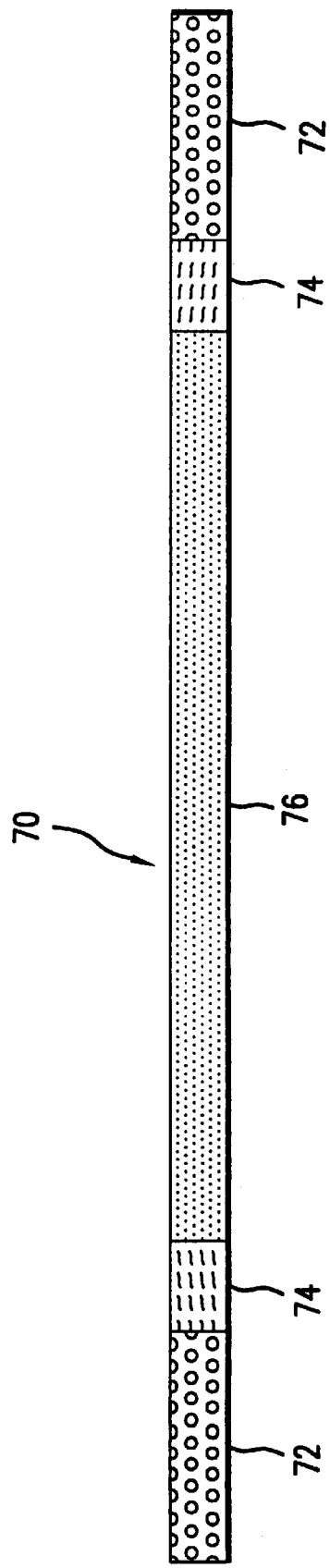
FIG. 3 illustrates a front, schematic view in elevation of a blood sample collected in accordance with the process of the invention.
Figure 4C:
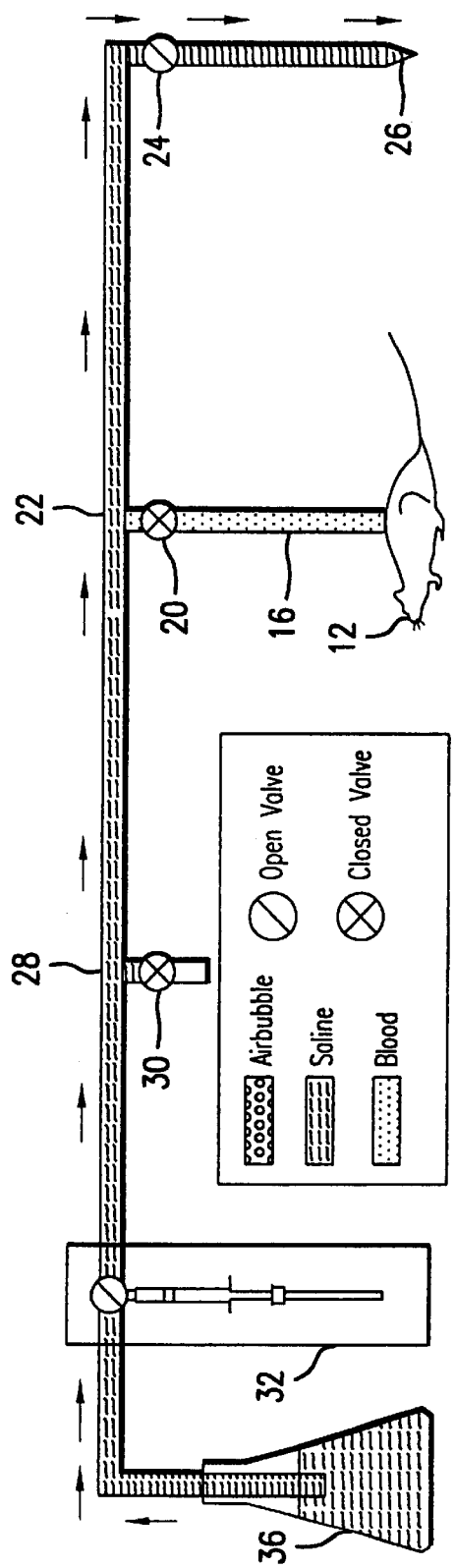
FIGS. 4a–n illustrates a series of front views in elevation of a process for collecting a blood sample.
Figure 4D:
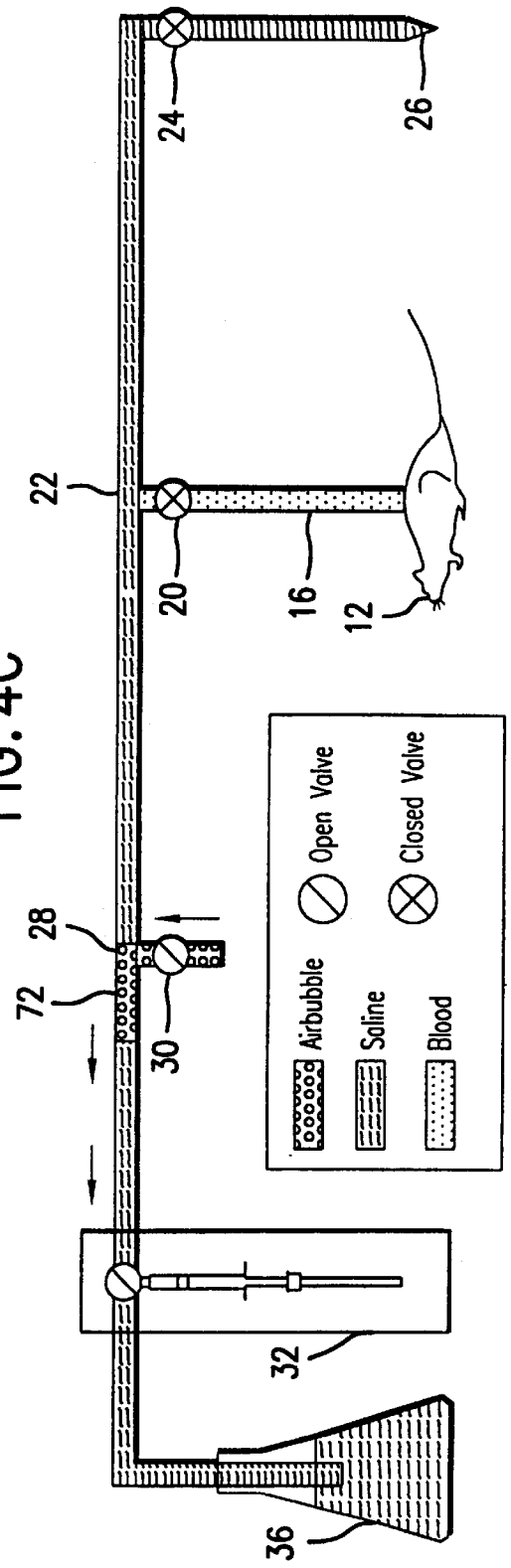
Figure 4E:
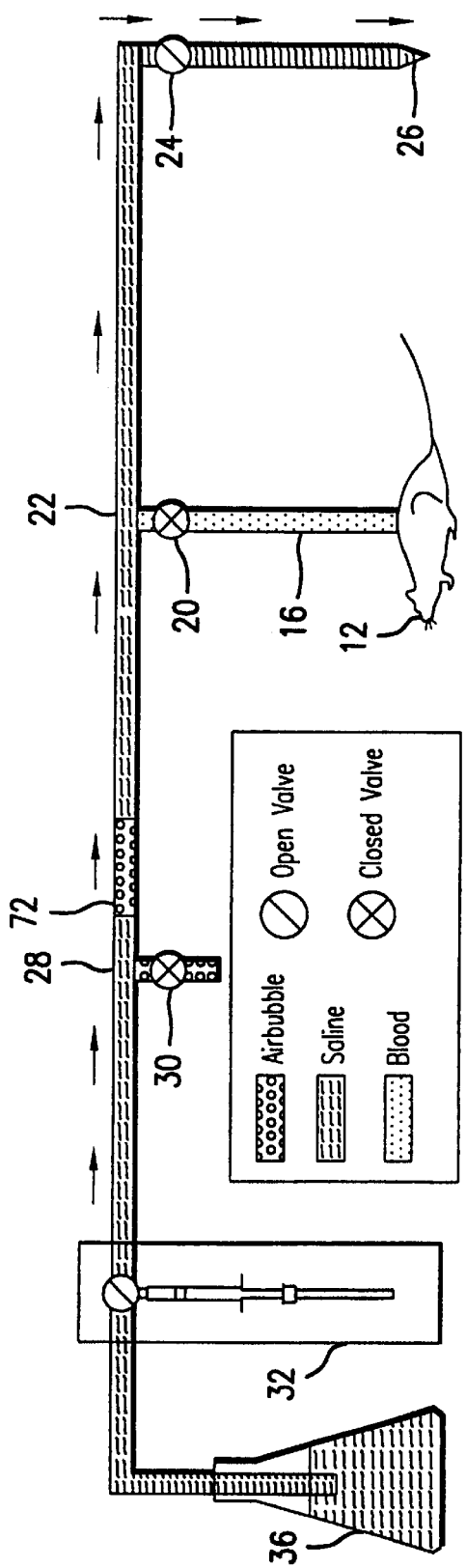
Figure 4F:
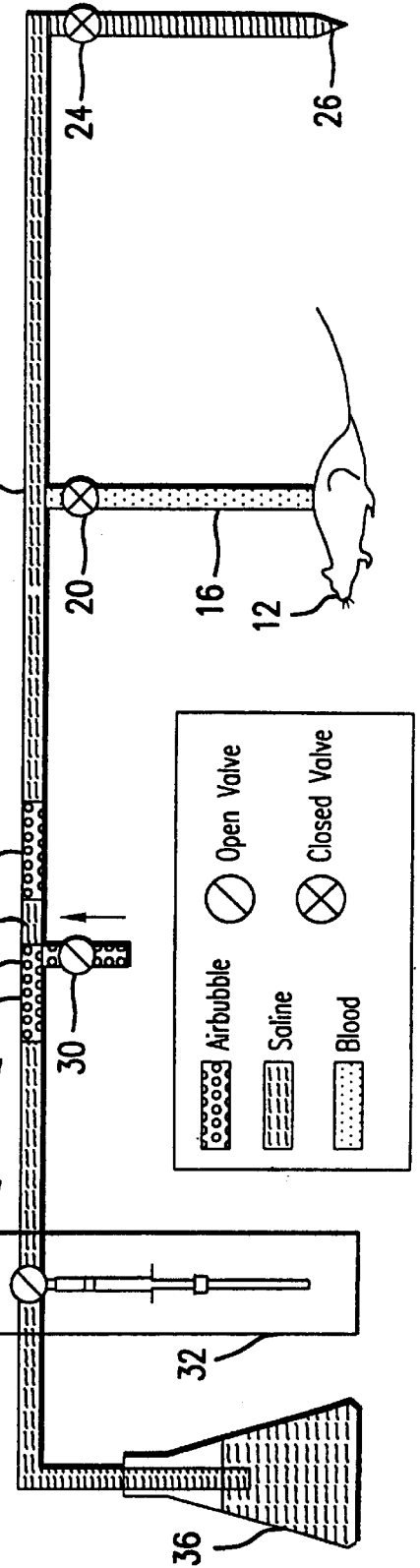
Figure 4G:
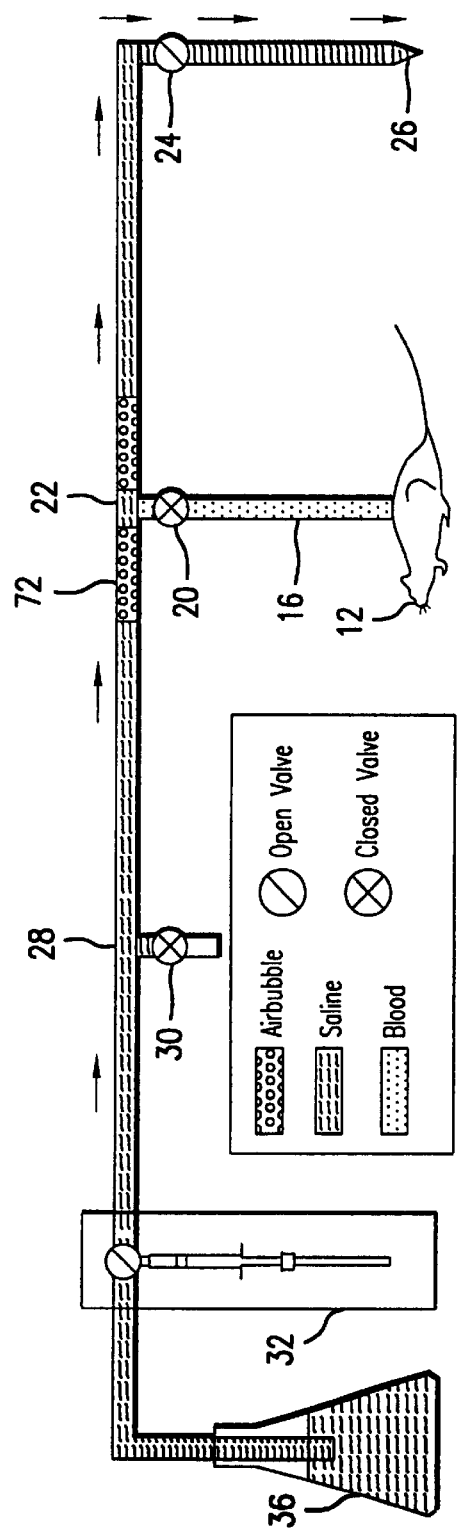
Figure 4H:
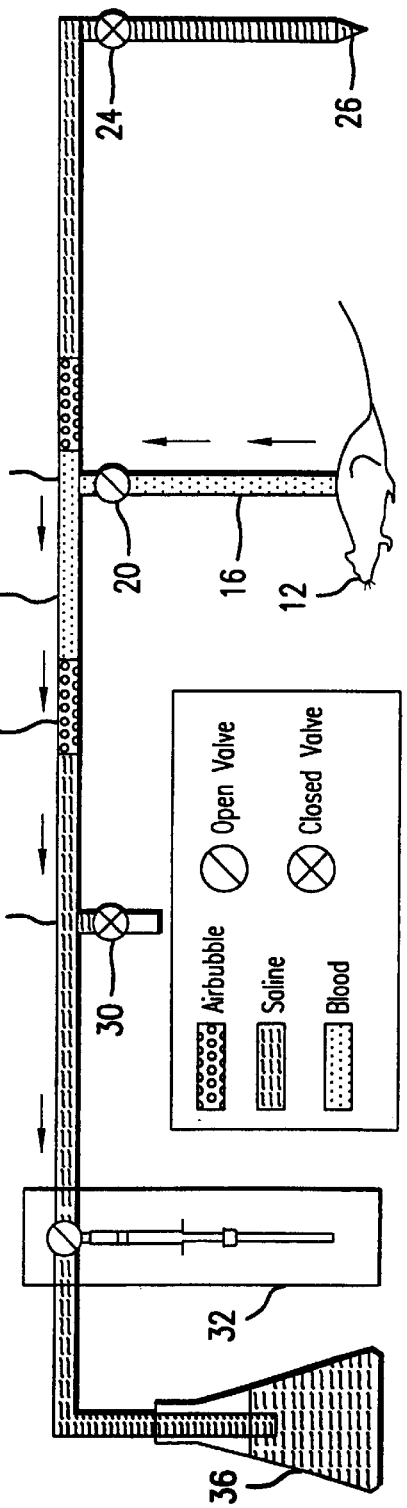

In FIG. 3, there is illustrated an air-saline-blood-saline-air unit-volume (70) generated within the tubing as representative of the blood sample collected from the animal during operation of the apparatus. While other benefits might exist, it is believed that the introduction of air bubbles (at least one air bubble at each end of the unit-volume) acts as a barrier for the additional dilution of the saline-blood-blood unit-volume with saline. Optionally, the apparatus of the present invention can be designed to generate an air-blood-air unit-volume if desirable, as will become apparent to one skilled in the art after reading this disclosure.

Generally, the blood sample is diluted with heparinized saline solution, equal to an amount desired for storage of the sample. Generally, the volume of blood removed from an animal as blood sample will be replaced within the animal blood system by an equal volume of saline solution during the sampling process. The three-phased, blood sample, comprising air, saline solution and blood, is characterized by air bubbles (72) being exterior to saline solutions (74), and the center of the sample being blood (76). Typically, the saline-blood-saline portion of the sample will be diffused within one another, i.e. the blood and saline phases will co-mingle. Since many blood samples are diluted with saline solution to prevent decomposition and dehydration during storage, a novel process of the invention incorporates the saline solution into the sample during the collection process. Furthermore, the air bubbles on either side of the sample, unit-volume act as a barrier to prevent further dilution of the sample with saline solution during transfer through the tubing and discharge thereof into the collection vial. In addition, the air bubbles prevent the deposition of blood, boundary layer on the inside of the tubing.

Generally, referring to FIG. 4, there is illustrated several process steps, a) through m), for collecting blood samples for a catheterized animal utilizing the novel apparatus of the invention. Catheterized animal (12) is placed into a metabolic cage, and connected to a cannula (16), pre-filled with heparinized saline solution. As shown in FIG. 4(a), air valve (30) and cannula valve (20) are closed, outlet valve (24) is opened, multi-port, programmable valve is opened to saline source (36), and syringe pump (32) is activated to push saline solution into the tubing. In accordance with FIG. 4(b), after outlet valve (24) is closed and cannula valve (20) is opened, syringe pump (32) is reversed to aspire or draw all the saline solution from cannula (16) into the tubing, wherein blood is withdrawn from animal (12) into cannula (16). Referring to FIG. 4(c), cannula valve (20) is closed, outlet valve (24) is opened, and the saline solution withdrawn from cannula (16) is purged from the tubing and replaced with fresh saline (74) withdrawn from saline source (36). FIG. 4(d) illustrates the opening of air valve (30), closing outlet valve (24), and aspiring air bubble (72) into air T-fitting (28). According to FIG. 4(e), air valve (30) is closed, outlet valve (24) opened, and saline solution (74) is use to push air bubble (72) forward towards cannula T-fitting (22) in the tubing. As provided in FIG. 4(f), air valve (30) is opened, outlet valve (24) is closed, and a second air bubble (72) is aspired into the tubing at air T-fitting (28). The volume of saline solution (74) between the bubbles being the volume of saline desired to dilute the sample for storage purposes. In accordance with FIG. 4(g), air valve (30) is closed, outlet valve (24) is opened, and the syringe pump is utilized to push the air bubbles (72) within the saline solution from the air T-fitting over the cannula T-fitting. After the saline-portion of the air-saline-air unit-volume is directly over the cannula valve, the cannula valve is open and the dispensing valve is closed, and with the syringe pump operating to aspirate or pull saline through the tubing, a desired volume of blood sample is collected into the saline phase of the air-saline-air unit-volume to generate blood sample (70), as shown in FIG. 4(h). Afterwards, as shown in FIG. 4(i), the syringe pump is deactivated, the cannula valve closed, the dispensing valve opened, and the pump re-activated to push blood sample (70) towards dispensing tip (26). Referring to FIG. 4(j), blood sample (70) is discharged from dispensing tip (26) into collection vial (78) for storage and analysis. After blood sample (78) is removed from dispensing tip (26), as illustrated in FIG. 4(k), air valve (30) is opened, outlet valve (24) is closed, and air bubble (72) is generated at air T-fitting (28) by aspiration. According to FIG. 4(l), air bubble (72) is pushed through the tubing toward cannula T-fitting (22) until it is a distance therefrom, the distance being equal to the volume of replacement saline necessary to replace the volume of sample removed from the animal. As shown in FIG. 4(m), outlet valve (24) is closed, cannula valve (20) is opened, and the syringe pump is activated to push the bubble (72) and replacement saline into cannula (16). Lastly, referring to FIG. 4(n), the syringe pump continues to push the replacement saline followed by air bubble (72) down through the cannula until the air bubble is just exterior to the animals body and the blood and saline are injected into the animal's blood system. When another sample is desired, the air bubble adjacent to the animal is drawn up the cannula until it reaches the cannula T-fitting, and the process cycle according to FIGS. 4(a) through 4(n) are repeated.

Another embodiment of the invention is directed to a process for automatically, repetitively sampling blood from a conscious animal utilizing the novel apparatus described herein above, the process characterized by the steps of:

a) closing the cannula and air valves, opening the outlet valve, and the first and second ports of the programmable valve to the saline source;

b) filling the tubing with heparinized, saline solution from the saline source utilizing the syringe pump to push the solution into the tubing;

c) attaching a catheterized animal to the cannula, wherein the cannula is pre-filled with saline solution;

d) closing the outlet valve, opening the cannula valve, and aspirating the saline solution from the cannula through the cannula T-fitting into the tubing in a direction towards the syringe pump until the saline in the cannula is in the tubing and a blood sample from the animal is drawn into the cannula;

e) closing the cannula valve, opening the outlet valve, and purging the tubing, through the dispensing tip of pre-filled saline solution, while filling the tubing with fresh, saline solution form the saline source;

f) closing the outlet valve, opening the air valve, and aspirating a first air bubble into the tubing at the air T-fitting;

g) closing the air valve, opening the outlet valve, and pushing the air bubble towards the cannula T-fitting;

h) closing the outlet valve, opening the air valve, and aspirating a second air bubble into the tubing followed by closing the air valve, wherein an air-saline-air phase is formed within the tubing, wherein a volume of saline between the air bubbles is equal to the volume of saline desired to dilute the sample;

i) closing the air valve, opening the outlet valve, and pushing the air-saline-air phase through the tubing, towards the cannula T-fitting so that the saline-portion of the phase is over the cannula T-fitting, wherein the tubing is filled with additional saline solution;

j) opening the cannula valve and activating the syringe pump to introducing an amount of blood sample into the saline-portion of the air-saline-air phase, wherein an air-saline-blood-saline-air phase is formed in the tubing;

k) closing the cannula valve, and pushing the air-saline-blood-saline-air phase through the tubing to the dispensing tip;

l) discharging the air-saline-blood-saline-air phase through the dispensing tip, into a vial of the fraction collector, wherein the tubing is filled with additional saline solution;

m) closing the outlet valve, opening the air valve, and aspiring an air bubble into the tubing at the air T-fitting;

n) closing the air valve, opening the outlet valve, and pushing the air bubble through the tubing proximal to the cannula T-fitting to form an air-saline phase adjacent to the cannula T-fitting, wherein a volume of saline in the tubing between the air bubble and the end of the cannula T-fitting connected to the cannula valve is equal to the volume of blood withdrawn from the animal; and o) closing the outlet valve, opening the cannula valve, said cannula being filled with blood, and pushing the air-saline phase and blood through the cannula into the animal, via the syringe pump, until the blood and saline are in the animal and the air bubble is adjacent to the outside of the animal;

wherein during collection of subsequent blood samples, steps a) through o) are repeated, wherein prior to repeating the steps, the air bubble adjacent to the animal and blood are raised to the cannula T-fitting and purged from the tubing with saline solution, and wherein the opening and closing of the valves, operation of the syringe pump and programmable valve are performed via computer control means.

The apparatus and process of the invention are suitable for collection of blood samples from small animals having a limited blood supply. Generally, no more than from about 10 to about 20 micro-liters ($\mu$l) blood samples are collected from small animals, e.g., mice, rats, hamsters, etc., per sample. Since the loss of blood from such small animals could be critical to normal metabolism, the present invention contemplates replacement of the sample with an equal volume of heparinized, saline solution. Typically, the 10 to 20 $\mu$l of blood sample can be diluted with from about 80 to about 100 $\mu$l of heparinized, saline solution prior to storage or analysis. The samples can be separately stored and analyzed or composites of an animal can be generated and stored for analyses according to methods known to those skilled in the art.

The means for confining a conscious animal generally include a metabolic cage or other surroundings, containing sufficient food and water, to prevent the animal from disconnecting the cannula. In one embodiment of the invention, a rigid material, metal wire or meshing can be placed around the cannula to prevent the animal from chewing through the cannula. Yet, in another embodiment of the invention, a fluid-swivel or similar device can be connected between the cannula and cannula valve to allow complete pivoting of the cannula as the animal moves about in the confining means. The confining means will generally comprise a cage with food and water sufficient to maintain the animal's normal metabolism.

The cannula and other tubing used to connect the components of the invention are generally constructed of a flexible polyethylene having an inside diameter of 0.03 inches and an outside diameter of 0.048 inches. The outlet, air and cannula pinch valves exhibit an inside diameter of 1/32 inches and an outside diameter of 3/32 inches and are marketed by Bio-Chem Valve Corp, Boston, Mass. The rigid stainless steel dispensing tip has an inside diameter of 0.023 inches and an outside diameter of 0.033 inches and is marketed by Small Parts, Miami Lakes, Fla. The syringe pump is marketed by Carro, Inc, Sunnyvale, Calif. The multi-port programmable valve is marketed by Carro, Inc.

What is claimed is:

1. An apparatus for automatically, repetitively sampling blood from a conscious animal, comprising:
   a) means for confining a conscious, catheterized animal;
   b) a cannula having first and second ends, said first end connected to the catheterized animal, said cannula being suitable for sampling blood from the animal;
   c) a cannula valve having first and second ends, said first end connected to the cannula, said cannula valve opening and closing being computer controlled;
   d) a cannula T-fitting having first, second and third ends, said first end connected to the second end of the cannula valve;
   e) an outlet valve having first and second ends, said first end connected, via tubing, to the second end of the cannula T-fitting, said outlet valve opening and closing being computer controlled;
   f) a dispensing tip having first and second ends, said first end connected to the second end of the outlet valve, said second end being suitable for discharging blood into a sample, collection vial;
   g) means for horizontal and vertical movement of the dispensing tip, said means for movement being computer controlled;
   h) an air T-fitting having first, second and third ends, said first end connected to the third end of the cannula T-fitting;
   i) an air valve having first and second ends, said first end connected to the second end of the cannula T-fitting, said second end connected to a check valve;
   j) a syringe pump suitable for transferring blood and saline solution through the apparatus, said pump having first and second ends, said first end connected, via tubing, to the third end of the air T-fitting, said pump being computer controlled;
   k) a rotary, programmable valve having four ports for receiving and discharging fluids, wherein the ports open and close by computer control, said first port being connected, via tubing, to the second end of the syringe pump;
   l) a heparinized saline source comprising a saline solution, said saline source being connected to the second port of the programmable valve;
   m) a fraction collector, comprising:
      i) a base having two horizontally opposed, parallel tracks, and a single track horizontally positioned above and perpendicular to the horizontally opposed, parallel tracks,
      ii) a temperature controlled rack in slidable contact with the horizontally opposed, parallel tracks,
      iii) means for sliding the rack along the tracks, said means being computer controlled, and
      iv) a plurality of sample, collection vials removably located in the rack, said vials being suitable for receiving samples from the dispensing tip; and
   n) computer means for accepting timing commands for collecting samples from the animal in coordination with the opening and closing of valves, sliding of the temperature controlled rack, pumping of the syringe pump, and dispensing samples into the collection vials, wherein samples can be collected at predetermined time intervals.

2. The apparatus according to claim 1, wherein a water source is connected to the third port of the multi-port valve.

3. The apparatus according to claim 2, wherein an acid wash source is connected to the third port of the multi-port valve.

4. The apparatus according to claim 3, wherein the saline source comprises a heparinized saline solution.

5. The apparatus according to claim 4, wherein the acid source comprises from about 0.1 to about 1.0 weight percent of a hydrochloric acid solution, based on 100 weight percent total.

6. The apparatus according to claim 5, wherein the computer means further comprises an input/out interface card for operation of the cannula, outlet and air valves, and fraction collector.

7. The apparatus according to claim 6, wherein a swivel is connected between the cannula and the cannula valve.

8. An apparatus for automatically, repetitively sampling blood from a plurality of conscious animals, comprising:
   a) means for individually confining a plurality of conscious, catheterized animals;
   b) a plurality of cannulae, each cannula having first and second ends, said first end connected to the catheterized animal;
   c) a plurality of cannula valves, each valve having first and second ends, said first end being connected to each cannula, said cannula valves' opening and closing being computer controlled;
   d) a plurality of cannula T-fittings, each valve having first, second and third ends, said first end being connected to the second end of each cannula valve;
   e) a plurality of outlet valves, each valve having first and second ends, said first end being connected to the second end of each cannula T-fitting, said outlet valves' opening and closing being computer controlled;
   f) a plurality of dispensing tips, each tube having first and second ends, said first end being connected to the second end of each outlet valve, said second end being suitable for discharging blood into a sample, collection vial;
   g) means for horizontal and vertical movement of the dispensing tip in and out of the collection vial, said means for movement being computer controlled;
   h) a plurality of air T-fittings, each valve having first, second and third ends, said first end being connected to the third end of the cannula T-fitting;
   i) a plurality of air valves, each valve having first and second ends, said first end being connected to the second end of each air T-fitting, said air T-fittings' opening and closing being computer controlled;
   j) a plurality of syringe pumps, each pump having first and second ends, said first end being connected to the third end of each air T-fitting, wherein the pumps are suitable for pumping blood and saline through the apparatus, said pumps being computer controlled, wherein each series of a) through j) components, comprise a separate sampling channel within the apparatus;
   k) a rotary, multi-port, programmable valve, each port suitable for receiving and discharging fluids, said first port being connected to the second end of the syringe pump, optionally the second end of a plurality of syringe pumps connected to a first end of a common manifold having first and second ends, and the second end of the manifold connected to the first port of the programmable valve, each port's opening and closing being computer controlled;

l) a saline solution source connected to the second port of the programmable valve;

m) a fraction collector, comprising:
  i) a base having two horizontally opposed, parallel tracks, and a single track horizontally located above and perpendicular to the horizontally opposed, parallel tracks,
  ii) a temperature controlled rack in slidable contact with the horizontally opposed, parallel tracks,
  iii) means for sliding the rack along the tracks, said means for sliding the rack being computer controlled, and
  iv) a plurality of sample, collection vials removably arranged in the rack, said collection vials being suitable for receiving a sample from the dispensing tip; and n) computer control means for programming and coordinating the operation of the collector, valves and pumps to collect blood samples at desired intervals,
wherein the valves, syringe pump, and fraction collector functions are coordinated and controlled by the computer means to withdraw samples from the animal at repetitive, programmable intervals and discharge the samples in collection vials.

9. The apparatus according to claim 8, wherein a water source is connected to the third port of the programmable valve.

10. The apparatus according to claim 9, wherein an acid wash source is connected to the fourth port of the programmable valve.

11. The apparatus according to claim 10, wherein a swivel is connected between the cannula and the cannula valve, said swivel being for pivotal movement of the cannel.

12. The apparatus according to claim 11, wherein a waste removal system is incorporated into the apparatus, said waste removal system comprising a dispensing tip manifold for receiving the dispensing tips, a waste collection trap connected to said manifold, a safety trap connected to said waste collection trap, and a vacuum means connected to said safety trap, said vacuum means for removing waste fluids from the dispensing tip.

13. The apparatus according to claim 12, wherein the dispensing tip manifold comprises a base having a plurality of vertical holes therethrough, each hole for receiving a dispensing tip, and a single hole horizontal hole intersecting with each vertical hole, said vertical hole for the passage of air associated with the vacuum means.

14. The apparatus according to claim 13, wherein the cannula, outlet and air valves are selected from the group consisting of pinch and check valves.

15. The apparatus according to claim 14, wherein cannula, outlet and air valves are interfaced with an input/output controller prior to connecting to the computer means.

16. The apparatus according to claim 15, wherein the slidable, fraction collector is interfaced with an input/output controller prior to connecting to the computer means.

17. The apparatus according to claim 16, wherein the saline source comprises a heparinized saline solution.

18. The apparatus according to claim 17, wherein a water source is connected to the third port of the programmable valve.

19. The apparatus according to claim 18, wherein an acid wash source is connected to the fourth port of the programmable valve.

20. The apparatus according to claim 19, wherein the acid wash source comprises from about 0.1 to about 1.0 weight percent of a hydrochloric acid solution, based on 100 weight percent total.

21. The apparatus according to claim 20, wherein an air-saline-blood-saline-air phase is generated in the apparatus.

22. The apparatus according to claim 21, wherein the air-saline-blood-saline-air phase is the blood sample.

23. The apparatus according to claim 22, wherein the saline-blood-saline portion of the sample is diffused.

24. A process for automatically, repetitively sampling blood of a conscious animal, utilizing the apparatus according to claim 1, comprising the steps of:
  a) closing the cannula and air valves, opening the outlet valve, and the first and second ports of the programmable valve to the saline source;
  b) filling the tubing with heparinized, saline solution from the saline source utilizing the syringe pump to push the solution into the tubing;
  c) attaching a catheterized animal to the cannula, wherein the cannula is pre-filled with saline solution;
  d) closing the outlet valve, opening the cannula valve and aspiring the saline solution from the cannula through the cannula T-fitting into the tubing in a direction towards the syringe pump until the saline in the cannula is in the tubing and a blood sample form the animal is drawn into the cannula;
  e) closing the cannula valve, opening the outlet valve, and purging the tubing, through the dispensing tip of pre-filled saline solution, while filling the tubing with fresh, saline solution form the saline source;
  f) closing the outlet valve, opening the air valve, and aspiring a first air bubble into the tubing at the air T-fitting;
  g) closing the air valve, opening the outlet valve, and pushing the air bubble through the tubing towards the cannula T-fitting;
  h) closing the outlet valve, opening the air valve, and aspiring a second air bubble into the tubing followed by closing the air valve, wherein an air-saline-air phase is formed within the tubing, wherein the volume of saline between the air bubbles is equal to the volume of saline desired to dilute the sample;
  i) closing the air valve, opening the outlet valve, and pushing the air-saline-air phase through the tubing, towards the cannula T-fitting so that the saline-portion of the phase is over the cannula T-fitting, wherein the tubing is filled with additional saline solution;
  j) opening the cannula valve and activating the syringe pump to introducing an amount of blood sample into the saline-portion of the air-saline-air phase, wherein an air-saline-blood-saline-air phase is formed in the tubing;
  k) closing the cannula valve, and pushing the air-saline-blood-saline-air phase through the tubing to the dispensing tip;
  l) discharging the air-saline-blood-saline-air phase through the dispensing tip, into a vial of the fraction collector, wherein the tubing is filled with additional saline solution;
  m) closing the outlet valve, opening the air valve, and aspiring an air bubble into the tubing at the air T-fitting;

n) closing the air valve, opening the outlet valve, and pushing the air bubble through the tubing proximal to the cannula T-fitting to form an air-saline phase adjacent to the cannula T-fitting, wherein a volume of saline in the tubing between the air bubble and the end of the cannula T-fitting connected to the cannula valve is equal to the volume of blood withdrawn from the animal; and o) closing the outlet valve, opening the cannula valve, said cannula being filled with blood, and pushing the air-saline phase and blood through the cannula into the animal, via the syringe pump, until the blood and saline are in the animal and the air bubble is adjacent to the outside of the animal;

wherein during collection of subsequent blood samples, steps a) through o) are repeated, wherein prior to repeating the steps, the air bubble adjacent to the animal and blood are raised to the cannula T-fitting and purged from the tubing with saline solution, and wherein the opening and closing of the valves, operation of the syringe pump and programmable valve are performed via computer control means.

25. The process according to claim 24, wherein the blood sample comprises an air-saline-blood-saline-air phase.

26. The apparatus according to claim 25, wherein the saline-blood-saline portion of the sample is diffused.

* * * * *